United States Patent [19]

Bogeso

[11] 4,235,916
[45] Nov. 25, 1980

[54] 2-METHYLTHIO-6-FLUORO-9-(1-METHYL-4-PIPERIDYLIDENE)-THIOXANTHENE AND SALTS THEREOF, NEUROLEPTIC COMPOSITIONS AND METHOD OF USE

[75] Inventor: Klaus P. Bøgesø, Kgs. Lyngby, Denmark

[73] Assignee: Kefalas A/S, Copenhagen-Valby, Denmark

[21] Appl. No.: 971,509

[22] Filed: Dec. 20, 1978

[30] Foreign Application Priority Data

Dec. 29, 1977 [GB] United Kingdom ............... 54175/77

[51] Int. Cl.³ ................. A61K 31/445; C07D 417/04; A61K 31/38
[52] U.S. Cl. ...................................... 424/267; 546/202
[58] Field of Search ......................... 546/202; 424/267

[56] References Cited

U.S. PATENT DOCUMENTS 4,086,350  4/1978  Zirkle .................................. 546/202

FOREIGN PATENT DOCUMENTS 835224   5/1976  Belgium ................................. 546/202
1453828 10/1976  United Kingdom ................... 546/202

OTHER PUBLICATIONS

Janssen et al., "Arzneimittelforschung", vol. 17, pp. 841–854, (1967).
Creese et al., "Science", vol. 192, pp. 481–483, (1976).
Roos et al., "Life Sciences", vol. 3, pp. 351–360, (1964).

Primary Examiner—Henry R. Jiles
Assistant Examiner—Robert T. Bond
Attorney, Agent, or Firm—Gordon W. Hueschen

[57] ABSTRACT

The present invention relates to the novel compound 2-methylthio-6-fluoro-9-(1-methyl-4-piperidylidene)-thioxanthene of the formula

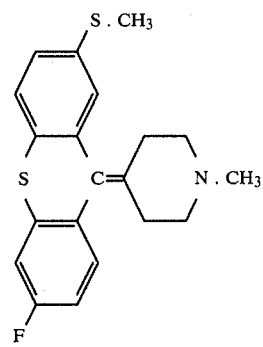

and its non-toxic acid addition salts, which compounds have strong and longlasting neuroleptic properties and, at the same time, a low degree of undesired side effects such as extrapyrimidal side effects.

The invention moreover relates to a method for the preparation of said novel compounds, pharmaceutical compositions containing same, which may be administered to animals, including human beings, orally or parentally.

Further the invention relates to a method for producing an antipsychotic effect in warmblooded animals by administering to said animals an antipsychotically effective amount of one of said novel compounds.

9 Claims, No Drawings

2-METHYLTHIO-6-FLUORO-9-(1-METHYL-4-PIPERIDYLIDENE)-THIOXANTHENE AND SALTS THEREOF, NEUROLEPTIC COMPOSITIONS AND METHOD OF USE

BACKGROUND OF THE INVENTION

In the past, several drugs having a tricyclic structure have been found useful in the treatment of severe psychotic disorders, especially of the schizophrenic type.

Some of the drugs are thioxanthenes which are substitued in the 2-position of one of the benzene rings, and some of the most active are described in U.S. Pat. No. 3,116,291. Recently, some thioxanthenes having a fluoro atom in the 6-position have been described, for example in British Pat. No. 1,453,828, as having neuroleptic properties of the same level as the known thioxanthene-neuroleptics but a much lower level of pharmacological effects associated with extrapyrimidal symptoms.

Further, some piperidylidene-thioxanthene derivatives having almost no extrapyrimidal side effects have been described in Belgian Patent No. 835,224. However, the said known thioxanthene compounds which have the lowest extrapyrimidal side effects also have relatively short-acting neuroleptic effects.

SUMMARY OF THE INVENTION

According to the present invention it has now surprisingly been found that the compound 2-methylthio-6-fluoro-9-(1-methyl-4-piperidylidene)-thioxanthene, as well as its non-toxic acid addition salts have both strong and relatively longlasting neuroleptic effects and, at the same time, a pharmacological profile which indicates low extrapyrimidal side effects when they are evaluated according to standard reliable published test methods. They also have a low acute toxicity compared with related thioxanthene derivatives, which makes the therapeutic index favorable. Moreover, they have strong anticholinergic effects.

This invention also includes pharmaceutically acceptable salts of 2-methylthio-6-fluoro-9-(1-methyl-4-piperidylidene)-thioxanthene formed with non-toxic organic acids. Such salts are easily prepared by methods known to the art. The base is reacted with either the calculated amount of organic or inorganic acid in an aqueous miscible solvent, such as acetone or ethanol, with isolation of the salt by concentration and cooling or an excess of the acid in aqueous immiscbile solvent, such as ethyl ether or chloroform, with the desired salt separating directly. Exemplaries of such organic salts are those with maleic, fumaric, benzoic, ascorbic, embonic, succinic, oxalic, bis methylene-salicylic, methanesulfonic, ethanedisulfonic, acetic, propionic, tartaric, salicylic, citric, gluconic, laetic, malic, mandelic, cinnamic, citraconic, aspartic, stearic, palmitic, itaconic, glycolic, p-aminobenzoic, glutamic, benzene sulfonic and theophylline acetic acids as well as the 8-halotheophyllines, for example 8-bromotheophylline. Exemplaries of such inorganic salts are those with hydrochloric, hydrobromic, sulfuric, sulfamic, phosphoric and nitric acids. Of course, these salts may also be prepared by the classical method of double decomposition of appropriate salts, which is wellknown to the art.

The novel compounds of the invention may be administered both orally and parenterally, for example in the form of tablets, capsules, powders, syrups, suppositories or solutions for injection.

According to the method of the invention 2-methylthio-6-fluoro-9-(1-methyl-4-piperidylidene)-thioxanthene and its non-toxic acid addition salts are prepared by dehydrating 2-methylthio-6-fluoro-9-(1-methyl-4-piperidylidene)-thioxanthen-ol-9 and isolating 2-methylthio-6-fluoro-9-(1-methyl-4-piperidylidene)-thioxanthene as the free base or a non-toxic acid addition salt thereof.

The dehydration according to the method of invention is preferably carried out by means of a mixture of glacial acetic acid and concentrated hydrochloric acid. Other dehydrating agents may, however, be used with satisfactory results, such as hydrochloric acid in chloroform, formic acid, phosphorous oxychloride, p-toluene sulfochloride, sulfuric acid, zinc chloride, potassium bisulfate, and the like, in inert organic solvents, e.g. chloroform and methylene chloride.

The starting material, which is a novel compound and forms part of the invention, may conveniently be prepared by cyclising 4-fluoro-2-(4-methylthiophenylthio)-benzoic acid (Collec.Czech. Chem.Commun, 40, p. 3523 (1975)) with phosphoric acid, and reacting the resulting 6-fluoro-2-methylthio-thioxanthone-9-one with a Grignard compound prepared from 4-chloro-1-methylpiperidine and magnesium, and hydrolysing the resulting Grignard complex with cold aqueous ammoniumchloride and isolating the resulting free base.

The following example is given to illustrate the method and products of the present invention but, it is to be understood as exemplary only and is not to be construed as limiting.

EXAMPLE

2-Methylthio-6-fluoro-9-(1-methyl-4-piperidylidene)-thioxanthene and its salts.

The starting material, 2-methylthio-6-fluoro-9-(1-methyl-4-piperidyl)-thioxanthen-9-ol, was prepared in the following way:

285 grams of 4-fluoro-2-(4-methylthiophenyl-thio)-benzoic acid (Collec. Czech. Chem. Commun, 40, p. 3523 (1975)) were added to 2 kilograms of polyphosphoric acid while stirring, and the mixture then warmed at 105 degrees Centigrade for 3 hours. The reaction mixture was then poured unto ice, stirred and the precipitate filtered off, washed with water and then suspended in a mixture of acetone and water. The suspension was made alkaline with 25% aqueous ammonia, filtered and the solid material dried. It consisted of 270 grams of crude 2-methylthio-6-fluoro-thioxanthene-9-one which after recrystallization from 250 milliliters of pyridine yilded 163 grams, which melted at 135-140 degrees Centigrade. Upon further recrystallization from pyridine 137 grams of almost pure 2-methylthio-6-fluoro-thioxanthene-8-one, which melted at 140-142 degrees Centigrade, were obtained.

To a Grignard-solution prepared from 130 grams of 4-chloro-1-methylpiperidine and 24 grams of magnesium turnings in 500 milliliters of dry tetrahydrofuran was added 174 grams of 2-methylthio-6-fluoro-thioxanthene-9-one in portions while stirring and cooling in an ice-salt mixture. The reaction temperature was kept below 10 degrees Centigrade. The cooling bath was then removed and the reaction mixture was stirred at 35-40 degrees Centigrade for 1.5 hours. The reaction mixture was then poured into a mixture of ice, water and ammonium chloride. The crystalline precipitate which was obtained upon cooling was sucked off, washed with water and dissolved in 10% aqueous acetic acid. The solution was treated with charcoal, extracted three times with 100 milliliters of ether and then made alkaline with 10 N sodium hydroxide solution. After cooling the precipitated base was sucked off, washed with water, suspended in 100 milliliters of acetone, filtered, again suspended in 100 milliliters of acetone, and then filtered and dried to yield 142 grams of 2-methylthio-6-fluoro-9-(1-methyl-4-piperidyl)-thioxanthen-9-ol which melted at 180-189 degrees Centigrade. The analytically pure compound melts at 192-195 degrees Centigrade after recrystallization from diethylether.

A solution of 140 grams of 2-methylthio-6-fluoro-9-(1-methyl-4-piperidyl)-thioxanthen-9-ol in 420 milliliters of glacial acetic acid and 420 milliliters of concentrated hydrochloric acid was refluxed for 1.5 hours, whereupon 250 milliliters of liquid were distilled from the reaction mixture. The reaction mixture was then poured unto crushed ice, made alkaline with concentrated aqueous ammonia and extracted with toluene. The toluene solution was separated, washed with water, and extracted with dilute acetic acid. The base was then liberated from the acid extract with concentrated aqueous ammonia and extracted with methylene chloride, which was dried over anhydrous potassium carbonate, filtered with charcoal, and concentrated in vacuo to yield 78 grams of base which was taken up in hexane and crystallized to give 70 grams of 2-methylthio-6-fluoro - 9 - (1 - methyl - 4 - piperidylidene) - thioxanthene which melted at 102-115 degrees Centigrade.

This product was purified by converting it to the oxalate, yielding 83 grams of oxalate melting at 212-218 degrees Centigrade (ethanol). The base was then liberated from the oxalate with dilute aqueous ammonia, extracted with methylene chloride, dried, filtered, concentrated in vacuo and crystallized from 96% ethanol to give 57 grams melting at 115-118 degrees Centigrade.

The pharmacological testing of 2-methylthio-6-fluoro-9-(1-methyl-4-piperidylidene)-thioxanthene, in the following called Lu 14-089 for short, and its non-toxic acid addition salts consisted of standard and reliable tests. Where the results with salts are compared with the results obtained with the free base it was found that the effect was the same as that obtained with the equivalent amount of free base.

The tests may be described as follows:

Determination of LD50 (mg/kg i.p.)

Mice, male, weighing from 18-25 g, fasted from 4 p.m. the day before test day.

Procedure

Four treated groups and one control group, each of 4 mice, are used.

The test substance is suspended in methyl cellulose 0.5% and injected intraperitoneally. The animals are placed in Macrolon cages type II. After 24 hours the number of deaths are counted and LD50 is determined according to a statistic table. Furthermore the results are recorded according to the punching instructions as fractions: 0/4, ¼, 2/4, ¾ and 4/4 where 0, 1, 2, 3 and 4 indicate the number of deaths after the dose in question.

Methylphenidate antagonism (ED50 mg/kg i.p.)

Perspex observation cages without bottom and lid, consisting of 5 sections each measuring $12 \times 25 \times 30$ cm. White corrugated paper. Mice, male, 18-25 g.

Dosage and procedure

The test substance is given i.p. in the doses 0, ⅛, 1/32 and 1/128 of the determined "i.p. LD50". $3 \times 2$ mice are used for each dose level. Two or 24 hours after injection of test substance, methylphenidate, 60 mg/kg, is injected s.c.

After administration of methylphenidate the mice are placed in the observation cages, 2 in each cage, where they remain for exactly 1 hour. The cages are placed on corrugated paper, the corrugations facing upwards. It is examined whether the mice have been biting the corrugated paper or not. If not, the substance has had an antagonistic effect. If one or more of the control pairs have not been biting, the test has to be repeated on a new set of mice.

The result is stated in fractions: 0/3, ⅓, ⅔ and 3/3 where 0, 1, 2 and 3 are the number of pairs which have not been biting on receipt of the dose in question. The results are calculated as the dose ($ED_{50}$), which causes antagonism in 50% of the test animals.

Amphetamine antagonism ($ED_{50}$ mg/kg i.p.)

Perspex observation cages without bottom and lid, consisting of 5 sections each measuring $12 \times 25 \times 30$ cm. White corrugated paper.
Rats, male, 230-270 g.

Dosage and procedure

The test substance is given i.p. in a reasonable dose based on the determined $LD_{50}$. Two hours later an intravenous injection of amphetamine sulphate 13.6 mg/kg ($\sim 10$ mg/kg amphetamine base) is given, after which the rats are placed individually in the cages. The cages are placed on white corrugated paper. Five rats are used for each dose level. Observations are made after 55 minutes and 65 minutes—observation time: 1 minute. The animals are observed for stereotypy (movements of the head, compulsive gnawing). If no stereotypy is demonstrated the substance has had an antagonistic effect. If the compound has full antagonistic effect another group of rats is used at a lower dose. If the compound shows no effect a higher dose is used. The result is stated as fractions: 0/5, 1/5, 2/5, 3/5, 4/5 and 5/5, where 0, 1, 2, 3, 4 and 5 indicate the number of rats which have not shown stereotypy at the dose in question. The results are calculated as $ED_{50}$ in mg/kg.

Catalepsy wire mesh, rat, max. ($ED_{50}$ mg/kg s.c.)

A vertical wire netting (50 cm $\times$ 49 cm). The meshes (openings) of the netting are square (1 cm $\times$ 1 cm). The wire diameter is 2 mm.
Stop watch.
Rats, male, 180-200 g.

Dosage and procedure

The animals are labeled and used in groups of five. The test substance is injected subcutaneously (s.c.) (5 ml/kg) at 4 dose levels selected from the fixed dose scale.

The animals are placed in the middle of the vertical wire netting 60, 120, 180, 240, 300 and 360 minutes after injection of the test compound. The animals are considered cetaleptic when they remain immobile during a period of 15 seconds. This cataleptic reaction is designated +. If the rats are "atonic" and passively slides down the wire mesh they are considered not cataleptic. If the animals climb up and down the wire mesh they are nor cataleptic. In both situations the designation − is used.

The results are recorded in fractions: 0/5, 1/5, 2/5, 3/5, 4/5 and 5/5, where 0, 1, 2, 3, 4 and 5 are the number of rats with designation + at the time where the dose in question possessed the strongest effect within the first 6 hours.

Physostigmine antagonism ($ED_{50}$ mg/kg i.p.)

Mice, male 20–25 g.
Scopolamine bromide 0.04 mg/ml or 0.1 mg/ml.
Physostigmine salicylate 0.2 mg/ml.
Macrolon cages type II.

Dosage and procedure

The test compound is injected i.p. in doses 0, ¼, 1/16 and 1/64 of the determined "i.p. LD50". Five mice are used for each dose level. One group, serving as positive control, is injected with scopolamine 0.4 mg/kg i.p. Thirty minutes after i.p. administration of test substance (or scopolamine), physostigmine 2 mg/kg, is injected i.p. This dose of physostigmine induces tremor with salivation, clonic convulsions, coma and death. After 60 minutes the number of survivors are counted.

The results are recorded in fractions: 0/5, 1/5, 2/5, 3/5, 4/5 and 5/5 where 0, 1, 2, 3, 4 and 5 inducate the number of animals in which the test compound has prevented the occurrence of death.

If scopolamine (positive control group) does not protect all physostigmine treated animals a new test should be made, and the results should not be recorded.

Muscarinic affinity binding

Rats, 150–200 g.
Sodium-phosphate buffer (pH 7.4). 15 mM (2.67 g $Na_2HPO_4$, $2H_2O$/1000 ml) and 100 mM (89 g $Na_2HPO_4$, $2H_2O$/5000 ml) 0.32 M sucrose (5.48 g/50 ml).
Sodium thiosulphate 10 mM (2.48 g/1000 ml) $^3$H-PrBCM (N-2′-chloroethyl-N-[2″, 3″-$^3$H$_2$] propyl-2-aminoethylbenzilate, spec. act. ~28 Ci/mM).

Procedure

A rat is killed by a blow on the head and exsanguinated. The whole brain is removed and homogenized in 10 volumes of ice cold 0.32 M sucrose with a hand homogenizer. The homogenate is centrifuged at 600 g for 10 minutes (4° C.) and the pellet discarded. The supernatant is then centrifuged at 25000 g for 55 minutes (4° C.). The pellet fraction ($P_2$) is resuspended in the same volume of 0.32 M sucrose as previously used and stored on ice.

The aziridinium ion of $^3$H-propylbenzilyllcholine mustard ($^3$H-PrBCM) is prepared by cyclization at a concentration of 130 nM in 15 mM Na-phosphate buffer (pH 7.4) for 50 minutes at 20° C. The reaction is terminated by addition of 100 volumes of ice cold buffer.

150 µl of the $P_2$-suspension are mixed with 1 ml of 100 mM phosphate buffer, preincubated for 10 minutes at 30° C. with test compound and then incubated with $^3$H-PrBCM to give a final concentration of about 9 nM. The incubation is continued for 15 minutes and stopped by addition of 20 ml 100 mM phosphate buffer containing 10 mM sodium thiosulphate. The samples are filtered through Whatman GF/C glass fiber filters and washed with 30 ml ice cold 100 mM phosphate buffer. The filters with synaptosomes are transferred to scintillation vials and the radio-activity measured by liquid scintillation counting after addition of 10 ml Instal-Gel (Packard Inst.). All experiments are performed in triplicate.

The results are recorded as mean percentage inhibition calculated by EDP on the basis of the level of a control group. Furthermore, the IC50 (the concentration which displaces specific $^3$H-PrBCM binding by 50%) is calculated. Specific $^3$H-PrBCM binding is defined as the total binding minus the binding in the presence of 20 µM atropine.

Apomorphine vomit

Adult Beagle dogs of either sex, housed individually in kennels or in cages.
2–4 dogs are used per dose level.

Dosage and procedure

The test compound is injected subcutanelusly in the back of the neck four hours before apomorphine, which is given intravenously in a dose of 25 µg/kg (volume 0.1 ml/kg). A control dog or a dog given an inactive dose of test compound will vomit in the course of few minutes after this threshold-dose of apomorphine.

Evaluation

The results are given as fractions, i.e. 0/2, ½ or 2/2, stating the number of dogs protected against vomiting over to the number of dogs. On account of the small number of animals the calculated $ED_{50}$ should be considered approximate.

Lu 14-089 was compared with the following substances:
2-Methylthio-9-(1-methyl-4-piperidylidene)-thioxanthene (Lu 14-145)
2-Trifluoromethyl-6-fluoro-9-(1-methyl-4-piperidylidene)-thioxanthene (Lu 12-312)
2-Trifluoromethyl-9-(1-methyl-4-piperidylidene)-thioxanthene (Lu 13-003)
2-Chloro-6-fluoro-9-(1-methyl-4-piperidylidene)-thioxanthene (Lu 12-304)
2-Chloro-9-(1-methyl-4-piperidylidene)-thioxanthene (Lu 13-016)

Further the following neuroleptic drugs designated by their INN-names (International Non-proprietary Names) were used as reference substances: flupentixol, clopenthixol, chlorprothixene, fluphenazine, chlorpromazine, haloperidal and clozapine.

The results obtained will appear from the following table:

| Substance | LD$_{50}$ | Methylphenidate antag. 2h | 24h | Amphetamine antag. | Catalepsy | Physostigmine antag. | Muscarine affinity | Ratio Catalep./ Amphetam. antag. | Apomorph. Vomit |
|---|---|---|---|---|---|---|---|---|---|
| Lu 14-089 | >320 | 0.10 | 14 | 0.74 | 6.3 | 7.2 | 14 | 8.5 | 0.014 |
| Lu 14-145 | 188 | 1.4 | 14 | >20 | >20 | 4.9 | 13 | ≳1 | — |
| Lu 12-312 | 188 | 0.07 | 2.1 | 0.56 | 0.067 | 7.7 | 18 | 0.12 | 0.04 |
| Lu 13-003 | 187 | 0.15 |  | 0.37 | 1.3 | 4.6 | 8 | 3.5 | — |
| Lu 12-304 | 187 | 4.6 |  | 5.5 | 3.4 | 8.9 |  | 0.62 | — |
| Lu 13-016 | 226 | 1.0 | >20 | 3.9 | 25 | 4.4 | 14 | 6.5 | — |
| flupentixol | 246 | 0.20 | >20 | 0.69 | 0.25 | >40 | 4000 | 0.36 | 0.02 |
| clopenthixol | 226 | 1.2 |  | 0.77 | 0.95 | >20 | 6000 | 1.2 | 0.04 |
| chlorprothixene | 226 | 0.71 | >20 | 6.1 | 4.0 | 86 | 110 | 0.66 | 0.90 |
| fluphenazine | 259 | 0.04 | 3.6 | 0.08 | 0.099 | >20 | 8000 | 1.2 | 0.007 |
| chlorpromazine | 226 | 4.0 | 20 | 7.1 | 5.6 | >40 | 1000 | 0.79 | 0.36 |
| haloperidol | 226 | 0.06 |  | 0.14 | 0.21 | >20 | 8600 | 1.5 | 0.010 |
| clozapine | >320 | >160 |  | >40 | 85 | 24 | 49 | <2.1 | about 4.0 |

As will be seen from the table Lu 14-089 has the most favourable ratio for catalepsy/amphetamine antagonism. While Lu 13-016 has a comparable ratio it has a much lower neuroleptic activity as expressed by the amphetamine antagonism and, at the same time, a higher acute toxicity.

Lu 14-089 as well as the non-toxic acid addition salts thereof may be administered to animals such as dogs, cats, horses sheeps or the like, including human beings, both orally and parenterally, and may be used for example in the form of tablets capsules, powders, syrups, suppositories, or in the form of the usual sterile solutions for injection. Results upon administration to human beings have been very gratifying.

Most conveniently the novel compounds of the invention are administered orally in unit dosage form such as tablets or capsules, each dosage unit containing one of the said compounds in an amount of from about 0.05 to about 50 mg, most preferably however, from about 0.5 to 25 mg, calculated as the free amine, the total daily dosage usually ranging from about 0.5 to about 300 mg. The exact individual dosages as well as daily dosages in a particular case will, of course, be determined according to established medical principles under the direction of a physician.

When preparing tablets, the active ingredient is for the most part mixed with ordinary tablet adjuvants such as corn starch, potato starch, talcium, magnesium stearate, gelatine, lactose, gums, or the like.

Typical examples of formulas for compositions containing Lu 14-089 as the active ingredient are as follows:
(1) Tablets containing 1 milligram of Lu 14-089 calculated as the free base in the form of the hydrochloride:
  Lu 14-089: 1 mg
  lactose: 37 mg
  potato starch: 74 mg
  gelatine: 2 mg
  talcum: 8 mg
(2) Solution for injection containing per ml:
  Lu 14-089, HCl: 0.55 mg
  sodium chloride: 9.0 mg
  sterile water ad 1 ml
(3) Syrup containing per milliliter:
  Lu 14-089: 0.2 mg
  methyl-paraben: 1.0 mg
  propyl-paraben: 0.1 mg
  saccharose: 400 mg
  water ad 1 ml
(4) Capsules containing per capsule:
  Lu 14-089: 2 mg
  lactose: 40 mg
  magnesium stearate: 0.5 mg Any other pharmaceutical tableting adjuvants may be used provided that they are compatible with the active ingredient, and additional compositions and dosage forms may be similar to those presently used for neuroleptics such as thiothixene, clopenthixol or flupentixol. Also combination of the novel compounds of the invention with other active inredients, especially other neuroleptics, thymoleptics, tranquilizers or the like, fall within the scope of the present invention.

As previously stated, when isolating Lu 14-089 in the form of an acid addition salt, the acid is preferably selected so as to contain an anion which is non-toxic and pharmacologically acceptable, at least in usual therapeutic doses. Representative salts which are included in this preferred group are the hydrochloride, hydrobromide, sulphate, acetate, phosphate, nitrate, methanesulphonate, ehtanesulphonate, lactate, citrate, tartrate or bitartrate, embonate and maleate of Lu 14-089. Other acids are likewise suitable and may be employed if desired, for example: Fumaric, benzoic, ascorbic, succinic, salicylic, bismethylenesalicylic, propionic, gluconic, malic, malonic, glycolic, benzenesulphonic, and sulphamic acids may also be emploued as acid addition saltforming acids.

When it is desired to isolate Lu 14-089 in the form of the free base, this may be done according to conventional procedure as by dissolving the isolated or unisolated salt in water, treating with a suitable alkaline material, extracting the liberated free base with a suitable organic solvent drying the extract and evaporating to dryness or fractionally distilling to effect isolation of the free basic amine.

The invention also comprises a method for the alleviation, palliation, mitigation or inhibition of the manifestations of certain physiological-psychological abnormalities of animals by administering to a living animal body, including human beings, an adequate quantity of Lu 14-089 or a non-toxic acid addition salt thereof. An adequate quantity would be from about 0.001 mg to about 1 mg per kg of body weight in each unit dosage and from about 0.003 milligrams to about 3 milligrams/kg of body weight per day.

It is to be understood that the invention is not limited to the exact details of operation or exact compound or compositions shown and described, as obvious modifications and equivalents will be apparent to one skilled in the art.

I claim:
1. A compound selected from the group consisting of (1) 2-methylthio-6-fluoro-9-(1-methyl-4-piperidylidene)-thioxanthene of the formula:

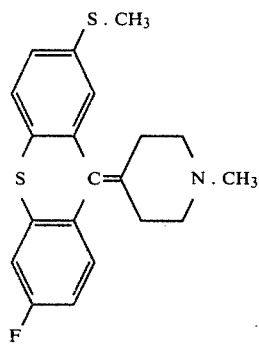

and (2) a non-toxic acid addition salt thereof.

2. A compound according to claim 1 which is 2-methylthio-6-fluoro-9-(1-methyl-4-piperidylidene)-thioxanthene.

3. A compound according to claim 1 which is the hydrochloride of 2-methylthio-6-fluoro-9-(1-methyl-4-piperidylidene)-thioxanthene.

4. A compound according to claim 1 which is the oxalate of 2-methylthio-6-fluoro-9-(1-methyl-4-piperidylidene)-thioxanthene.

5. A pharmaceutical composition in unit dosage form comprising as an active ingredient 2-methylthio-6-fluoro-9-(1-methyl-4-piperidylidene)-thioxanthene or a non-toxic acid addition salt thereof together with a pharmaceutical carrier or excipient.

6. A pharmaceutical composition according to claim 5 characterized thereby that each dosage unit contains the active ingredient in an amount ranging from 0.15 to 50 mg.

7. A compound of the formula:

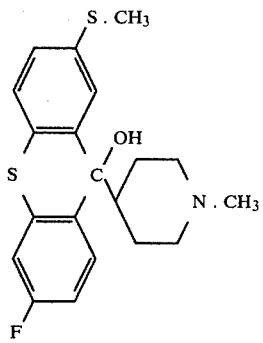

which is 2-methylthio-6-fluoro-9-(1-methyl-4-piperidylidene)-thioxanthen-ol-9.

8. The method of producing a neuroleptic effect in a warm-blooded animal, comprising the step of administering to the said warm-blooded animal an effective neuroleptic amount of a compound of claim 1.

9. The method of claim 8, wherein the compound is administered in an amount from about 0.003 milligrams to about 3 milligrams per kilogram of bodyweight per day.

* * * * *

UNITED STATES PATENT AND TRADEMARK OFFICE
CERTIFICATE OF CORRECTION

PATENT NO. : 4,235,916
DATED : November 25, 1980
INVENTOR(S) : Klaus P. Bøgesø

It is certified that error appears in the above-identified patent and that said Letters Patent are hereby corrected as shown below:

Title Page, line under "United States Patent [19]"; "Bogeso" should read
-- Bøgesø --
[75] Inventor; "Klaus P. ˙Bøgesø," should read -- Klaus P. Bøgesø, -- delete the top "˙" after the "P."
Col. 1, lines 12 & 13; "substitued" should read -- substituted --
Col. 2, line 46; "Centrigrade" should read -- Centigrade --
Col. 2, line 55; "Centrigrade" should read -- Centigrade --
Col. 3, line 47; "salts are" should read -- salts were --
Col. 5, line 66; "$^3$H-propylbenzilyllcholine" should read
-- $^3$H-propylbenzilylcholine --
Col. 7, line 46; "talcium," should read -- talcum, --
Col. 8, line 28; "inredients" should read -- ingredients --
Col. 8, line 38; "ehtanesulphonate," should read -- ethanesulphonate, --

UNITED STATES PATENT AND TRADEMARK OFFICE
CERTIFICATE OF CORRECTION

PATENT NO. : 4,235,916

DATED : November 25, 1980

INVENTOR(S) : Klaus P. Bøgesø

It is certified that error appears in the above-identified patent and that said Letters Patent are hereby corrected as shown below:

Col. 1, line 51; "immiscbile" should read -- immiscible --
Col. 1, line 66; "wellknown" should read -- well-known --
Col. 2, line 47; "unto" should read -- onto --
Col. 2, line 54; "yilded" should read -- yielded --
Col. 2, line 57; "-thioxanthene-8-one," should read -- -thioxanthene-9-one, --
Col. 3, line 22; "unto" should read -- onto --
Col. 5, line 1; "cetaleptic" should read -- cataleptic --
Col. 5, line 3; "slides" should read -- slide --
Col. 5, line 6; "are nor cataleptic." should read -- are not cataleptic. --
Col. 6, line 34; "subcutanelusly" should read -- subcutaneously --
Col. 8, line 44; "emploued" should read -- employed --
Col. 8, line 45; "saltforming" should read -- salt-forming --
Col. 8, lines 66 & 67; "medifications" should read -- modifications --

Signed and Sealed this

Twenty-third Day of June 1981

[SEAL]

Attest:

RENE D. TEGTMEYER

Attesting Officer

Acting Commissioner of Patents and Trademarks